United States Patent
Klewinghaus (10) Patent No.: US 9,695,957 B2
(45) Date of Patent: Jul. 4, 2017

(54) CONNECTING DEVICE WITH A CLAMPING DEVICE FOR CONNECTING TO AN ARRANGEMENT FOR CLOSING FLOW PATHS AND MONITORING THE STATUS OF THE CLAMPING DEVICE AND METHOD FOR SAME

(71) Applicant: Fresenius Medical Care Deutschland GmbH, Bad Homburg (DE)

(72) Inventor: Juergen Klewinghaus, Oberursel (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 630 days.

(21) Appl. No.: 14/171,104

(22) Filed: Feb. 3, 2014

(65) Prior Publication Data
US 2014/0216557 A1 Aug. 7, 2014

Related U.S. Application Data

(60) Provisional application No. 61/760,441, filed on Feb. 4, 2013.

(30) Foreign Application Priority Data

Feb. 4, 2013 (DE) .......... 10 2013 001 850

(51) Int. Cl.
| | |
|---|---|
| A61M 39/28 | (2006.01) |
| F16K 37/00 | (2006.01) |
| F16K 7/04 | (2006.01) |
| A61M 1/36 | (2006.01) |

(52) U.S. Cl.
CPC ......... *F16K 37/0091* (2013.01); *A61M 1/367* (2013.01); *A61M 1/3639* (2013.01); *A61M 39/28* (2013.01); *F16K 7/04* (2013.01); *F16K 37/0083* (2013.01); *A61M 2205/14* (2013.01); *A61M 2205/332* (2013.01); *Y10T 137/0318* (2015.04); *Y10T 137/8158* (2015.04); *Y10T 137/8225* (2015.04); *Y10T 137/8326* (2015.04)

(58) Field of Classification Search
CPC .......... F16L 55/10; A61M 39/10; A61M 1/14; A61M 1/36; A61M 1/367; A61M 1/3639; A61M 2205/14; A61M 2205/332; F16K 37/0091
See application file for complete search history.

(56) References Cited

U.S. PATENT DOCUMENTS

| | | |
|---|---|---|
| 5,445,613 A | 8/1995 | Orth |
| 5,614,677 A | 3/1997 | Wamsiedler et al. |
| 5,769,385 A | 6/1998 | Burrous et al. |
| 6,604,908 B1 | 8/2003 | Bryant et al. |
| 2003/0187379 A1 | 10/2003 | Sun |

(Continued)

FOREIGN PATENT DOCUMENTS

| | | |
|---|---|---|
| DE | 4419593 | 12/1995 |
| DE | 296 09 926 | 10/1996 |

(Continued)

*Primary Examiner* — Daniel Wiley
(74) *Attorney, Agent, or Firm* — Jacobson Holman, PLLC.

(57) ABSTRACT

A connecting device for connecting an external function device to an arrangement and for cutting off flow paths by accommodating a clamping device includes a pressure-measuring unit and/or a length-measuring unit configured to detect a clamping force and/or a distance such that it is possible to monitor the status of the clamping device.

15 Claims, 9 Drawing Sheets

(56) References Cited

U.S. PATENT DOCUMENTS

2012/0073673 A1  3/2012  Kameyama
2012/0141197 A1  6/2012  Lauer

FOREIGN PATENT DOCUMENTS

| DE | 19900320 | 7/2000 |
|----|----------|--------|
| DE | 103 29 159 | 1/2005 |
| DE | 102009036101 | 2/2011 |

CONNECTING DEVICE WITH A CLAMPING DEVICE FOR CONNECTING TO AN ARRANGEMENT FOR CLOSING FLOW PATHS AND MONITORING THE STATUS OF THE CLAMPING DEVICE AND METHOD FOR SAME

CROSS-REFERENCE TO RELATED APPLICATIONS

This application claim benefit to U.S. Provisional Application No. 61/760,441, filed Feb. 4, 2013.

BACKGROUND OF THE INVENTION

1. Field of Invention

The present invention relates to a connecting device for connecting an external function device having an arrangement for closing flow paths by accommodating clamping device and a pressure-measuring unit and/or a length-measuring unit for detecting a clamping force and/or a distance, thus making it possible to monitor the status of the clamping device.

2. Description of the Prior Art

Connecting devices for connecting an external function device to an arrangement for diagnostic and treatment methods and the like, such as those used in the medical technical field in particular, are known from the prior art. Such connecting devices are used in particular in arrangements for treating blood in extracorporeal blood circulations. The connecting devices are also equipped with various components which assign a defined functionality to the connecting devices. These components include, for example, sensors or actuators which fulfil a very specific function within the arrangement (for example, pressure measurement). In addition, the known arrangements also include clamping devices or valve devices for opening and closing fluid paths.

Additional clamping devices or valve, devices are often necessary within an arrangement for adaptation of novel, more complex treatment and diagnostic methods or the like.

It is a disadvantage that it is impossible to easily integrate additional clamping devices or valve devices into an existing device. Thus if all the clamping devices or valve devices present on the device side are occupied but additional clamping functions are needed, these methods cannot be applied to the existing arrangements. Another disadvantage is that the use of such methods can be implemented only through extensive structural and technical revision of the arrangement, which is extremely time-consuming and also expensive.

DE 10 2009 036 101 describes a connecting device for connecting at least one external function device to an arrangement by pressing the external function device between two contact points. The connecting device here is equipped with a pressure-measuring unit for measuring the pressure in a pressure-measuring device that represents the external function device. The defined function of measuring the pressure inside the arrangement is assigned to the connecting device through the combination of the pressure-measuring unit with the pressure-measuring device.

DE 44 19 593 describes a device for measuring a fluid pressure. The device, described here is equipped with a pressure-measuring unit to measure a fluid pressure inside a pressure-measuring device. Here again, the defined function of measuring the pressure is assigned to the connecting device in the combination with the Pressure-measuring unit and the pressure-measuring device.

SUMMARY OF THE INVENTION

The object of the present invention is to configure the connecting devices known from the prior art for connection so an arrangement in such a way as to make it possible to perform diagnostic and treatment methods and the like, on which more complex flow schemes are based. In addition, a flexible adjustment of the various methods to the existing arrangement and thus universal use of the arrangement are to be made possible through the adaptation of the connecting devices.

In addition, an inexpensive adaptation of more complex diagnostic and treatment methods or the like is to be made available for connecting the connecting device and for closing off flow paths in an existing arrangement. The adaptation to the respective method should be quick and reliable and easy to handle.

Another object of the present invention is to adjust components of the existing arrangement to permit monitoring of the open and/or closed status of flow paths.

In cases in which more than the available clamping devices or valve devices are needed in an arrangement but some of the existing connecting devices which originally had a different function (for example, measuring the pressure) are not needed, the object is to improve upon the connecting device, so that free unneeded connecting devices within an arrangement can assume another new or additional function instead of their original function.

This object is achieved by the subject matter of the invention described herein. An external function device is inserted into a connecting device for connecting an external function device to an arrangement comprising an accommodating unit to accommodate the external function device, an outer carrier, an essentially cylindrical inner carrier and a movable middle carrier, a pressure-measuring unit for measuring the pressure in an external function device and/or a length-measuring unit for measuring a distance, a force-transfer unit for continuous displacement of the movable middle carrier along the distance. The external function device is designed in the form of clamping devices or valve devices and is equipped with clamping elements for closing off a flow path.

By means of various components such as a pressure-measuring unit for detecting a clamping force or a closing force and/or a length-measuring unit for measuring a distance between a first end point and a second end point, these components can be adjusted to permit monitoring of the status of the clamping device.

Due to the use of an external function device in the form of clamping devices or valve devices, an inexpensive adaptation is made available for diagnostic and treatment methods or the like in connecting devices for connecting the connecting device and for closing off flow paths in an existing arrangement.

In an alternative embodiment, in addition to the clamping force or closing force and/or the distance, a pressure can be determined inside a fluid-carrying element of a clamping device or a valve device.

The connecting device configured in this way is then occupied with another new or additional functionality instead of its original function. The object according to the invention is also achieved by a method as described herein.

The object according to the invention is additionally achieved by a clamping or valve device, which is suitable for insertion and for functioning in the connecting device described herein.

Additional advantageous embodiments of the invention are derived from the associated description provided herein.

The phrase "complex diagnostic or treatments methods or the like" is to be understood to include those methods which require more clamping devices and/or valve devices than those present in the corresponding traditional arrangements because of their process-specific requirements.

The "external function devices" such as those used in the sense of the invention are clamping devices or valve devices with clamping elements and/or valve elements. The clamping devices or valve devices may preferably be designed as disposable items.

"Clamping devices or valve devices" are understood to be devices which are suitable for regulating or cutting off the flow of fluids.

The term "closing" is understood to refer to a reduction or complete interruption in a fluid flow in a fluid-carrying element in the sense of the invention.

An "arrangement" such as that used here may be a medical technical arrangement such as a blood treatment device, a dialysis device, in particular an apheresis or plasma apheresis device, an arrangement in laboratory technology, in the production of drugs or foods or the like.

The "connecting" according to the invention may refer to a functional and/or mechanical connection of the external function device in the, form of to clamping or valve device with an arrangement such that the clamping device is in contact with at least one measuring device on the side of the arrangement in order to determine a clamping force or a closing force and/or a distance.

A "force-transfer unit" such as that used here serves to transfer a force within an arrangement to components in the connecting device. The force may be transferred mechanically, pneumatically, hydraulically, electrically, electromagnetically, inductively or by any other suitable method.

The "components" for monitoring of state according to invention are primarily sensors or actuators, in particular measuring devices, for example pressure measuring devices and length measuring devices.

The "length measuring device" as used in the sense of the invention is mounted on the moving parts of the connecting device. In a special embodiment, this is in the outer carrier of the connecting device. In a movable middle carrier of the connecting device, an aperture by means of which a distance (S) can be detected using a light barrier is mounted so that various opening and closing states of the clamping device can be determined in this way.

The "pressure-measuring unit" as used here is primarily adopted so that it serves as a support for the clamping device in order to detect a clamping force and/or a closing force. The pressure-measuring unit may be used in combination with the status monitoring of the clamping device to measure a fluid pressure.

By adaptation of the clamping device, the arrangement may advantageously be used in a flexible and universal manner for a variety of diagnostic and treatment methods or the like, which require more clamping devices than the available ones in the arrangement. The adaptation of the connecting device in an arrangement to the respective specific requirements for a method with regard to the required clamping functions can be performed rapidly, easily and reliably. In addition, it is not necessary to perform any complex and cost-intensive structural measures on an arrangement.

BRIEF DESCRIPTION OF THE DRAWINGS

The various exemplary embodiments of the invention are explained in greater detail below with reference to the drawings.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
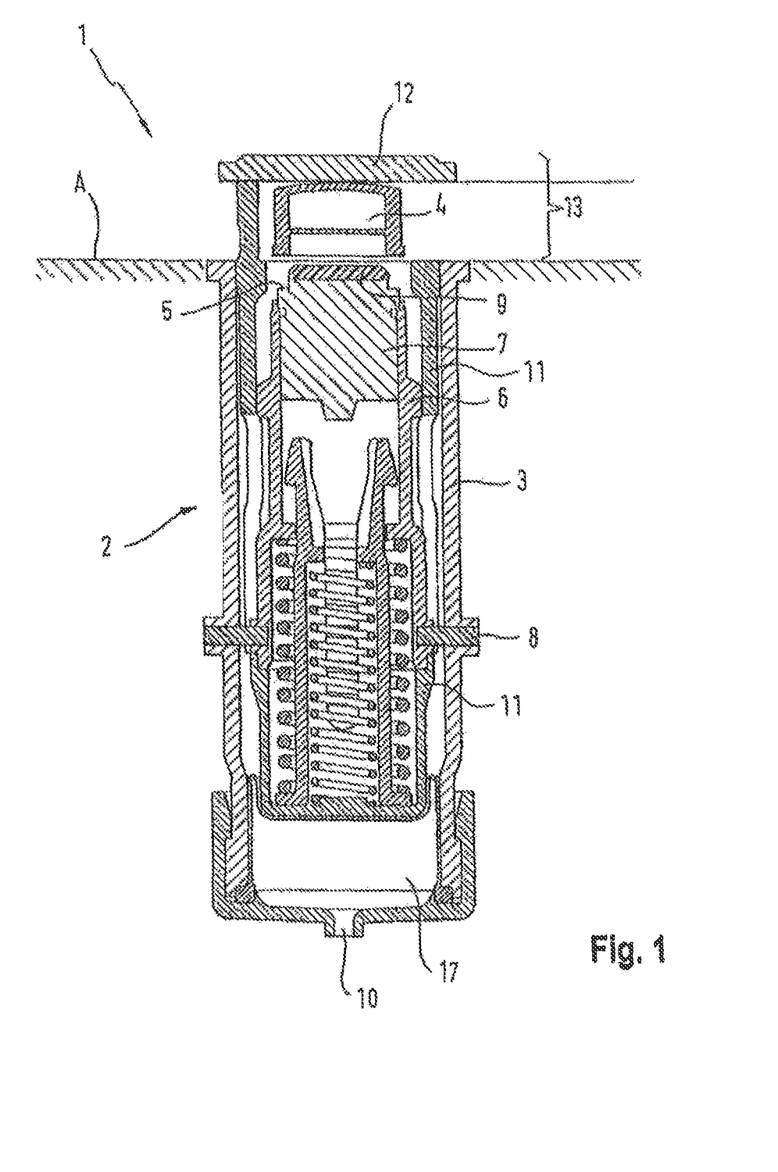
FIG. 1 shows a sectional diagram of a connecting device for connecting an external function device to an arrangement and an inserted external function device.

"Connecting devices" (2) such as those known from FIG. 1 contain three hollow bodies arranged one inside the other. The outermost of the three hollow bodies is referred to as the outer carrier (3). It may be rigid on the face, i.e., fixedly integrated into the interior of an arrangement (1), for example, a blood treatment machine, while being flange-connected at the height of a coupling face (A) for connecting an external function device (4).

The coupling face (A) is a section on the top side of an outer carrier (3), but it may also be an outer sensor surface or a protrusion (5) on a pressure-measuring unit (7) which is fixedly integrated with the inner carrier (6) or on any section that is suitable for a force pickup.

In the interior of the outer carrier (3), the essentially cylindrical inner carrier (6) is held coaxially with the outer carrier (3) by means of rigid radial connecting carriers (8). The pressure-measuring unit (7) with the pressure-sensitive membrane (9) carried by the inner carrier (6) is always arranged in the same position with respect to the coupling surface (A).

Between the outer carrier (3) and the inner carrier (6) a free uniform annular or tubular gap is provided. The free lower end of the outer carrier (3) shown in FIG. 1 is closed by a bottom and has a force-transfer connection (10).

An upper and a lower middle carrier (11) are provided as additional hollow bodies, arranged one inside the other. The lower middle carrier is shown as a spring dowel in FIG. 1. Each of these two hollow bodies is displaceable axially and separately from one another within the outer carrier (3). However, the middle carrier (11) may also be designed in one piece.

In the movable middle carrier (11), there is a recess below a pressure plate (12), said recess also being referred to as an accommodating device (13) and being provided for receiving the external function device (4).

Figure 2:
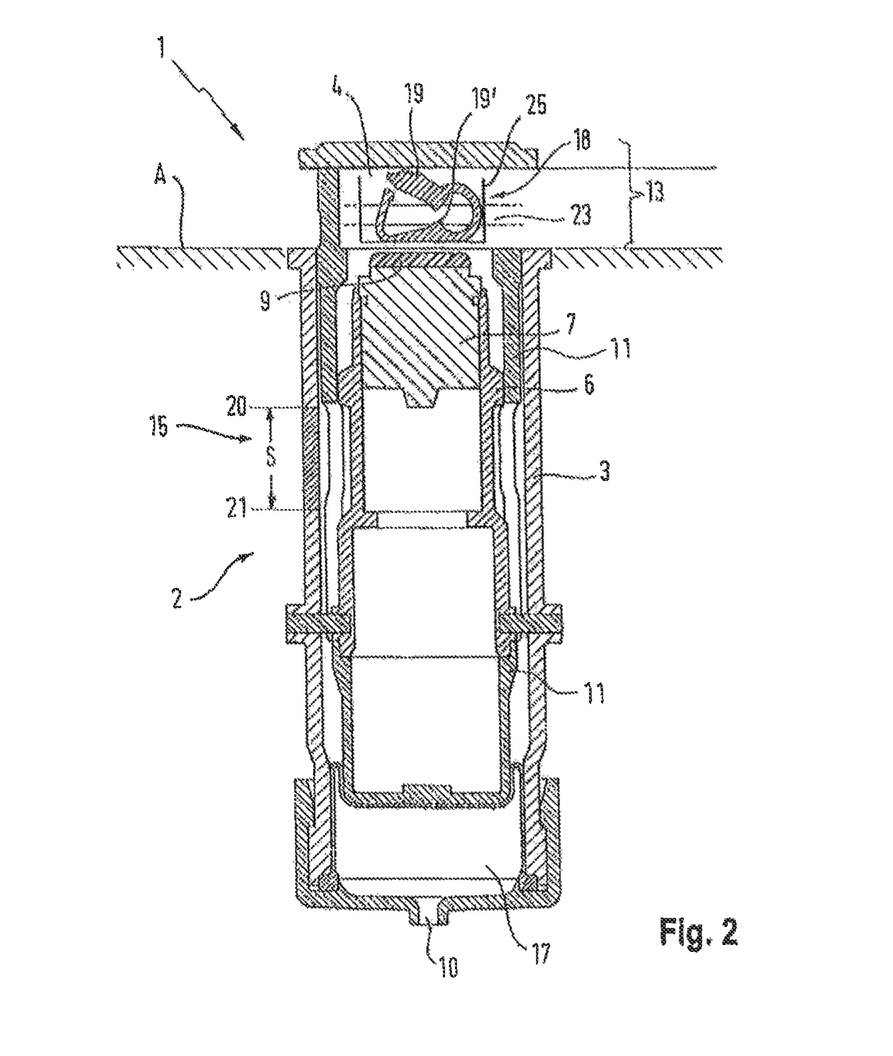
FIG. 2 shows a sectional diagram of a connecting device, having a clamping device as an external function device, which contains a clamping element in the form of an open hose clamp and a fluid-carrying element, for example.

FIG. 2 shows a connecting device (2) and is now shown as a clamping device or valve device (18) in the open state as an external function device (4), such that the clamping device (18) has a fluid-carrying element (23) and clamping elements (19).

To solve the problem according to the invention, the connecting device (2) for connecting an external function device (4) to an arrangement (1) contains:

an accommodating device (13) for accommodating the external function device (4),
an outer carrier (3), an essentially cylindrical inner carrier (6) and a movable middle carrier (11),
a pressure-measuring unit (7) for measuring the pressure in the external function device (4) and/or
a length-measuring unit (15) for measuring a distance (S),
a force-transfer unit (17) for continuous displacement of a movable middle carrier (11) along a distance (S), wherein the connecting device (2) is configured, so that the external function device (4) is equipped with a clamping device (18) for closing off a flow path, such that
the clamping device (18), which may also be referred to as a valve device, has clamping elements (19) and/or clamping prisms (19') or valves.

In addition:
the pressure-measuring unit (7) is adapted for detecting a clamping force or a closing force and/or
the length-measuring unit (15) is adapted for measuring a distance (S) between a first end point (20) and the second end point (21) to permit monitoring of the status of the clamping device (18).

For the status monitoring, a clamping force or a closing force and/or a distance (S) is/are detected and the opening status and/or closing status of the clamping devices (18) is/are determined by means of an analysis unit (no shown). In addition to monitoring whether the clamping device (18) is completely open or closed and thus whether the flow path is freely passable or closed, intermediate positions can also be detected.

The middle carrier (11) is displaced within the outer carrier (3) of the connecting device (2) by means of a force-transfer unit (17) to thereby be able to detect a force by means of the pressure-sensitive membrane (9) of the pressure-measuring unit (7) and/or a distance (S) by means of a length-measuring unit (15). The transfer of force may be accomplished pneumatically or hydraulically by means of a force transfer connection (10) in particular.

Figure 3A:
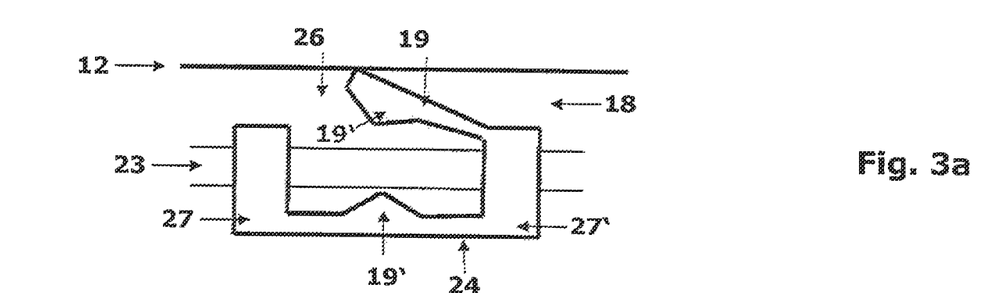
FIG. 3a to 3d show schematically different embodiments of clamping devices in the form of hose clamps in the open and closed state and with a structural limitation on the closing distance.

In a first embodiment of the clamping device (18), which is shown in FIG. 3a in the open state, it has a bottom side (24) bordered by a rigid bottom side and/or area, and it has a top side (26). The bottom side in the sense of the invention is the side facing the pressure-measuring unit (7), and the top side is the side facing the pressure plate (12). The top side (26) may be designed as an elastic and/or flexible lever or arm and may act as a clamping element (19). Clamping elements (19) on the bottom and/or top sides (24), (26) may also be designed as inwardly directed clamping prisms, clamping wedges, elevations, arches, mandrels or the like as moulded parts suitable for closing off a fluid-carrying element (23). For the sake of simplicity, only the concept of the clamping prisms (19') shall be used in the remaining description. The top side (26) may be designed to be open or closed. The clamping device (18) has two opposing side openings which serve as holders (27, 27') for the fluid-carrying element (23), The side holders (27, 27') of the clamping device (18) are in general designed to be rigid. The fluid-carrying element (23) is in particular a flexible tubing, which may be guided through the side holders (27, 27') of the clamping device (18).

The clamping device (18) may also be integrated into a housing (25) as shown in FIG. 2, The housing (25) also has two lateral holders (27, 27') as a passage or guide for the fluid-carrying element (23).

Figure 3B:
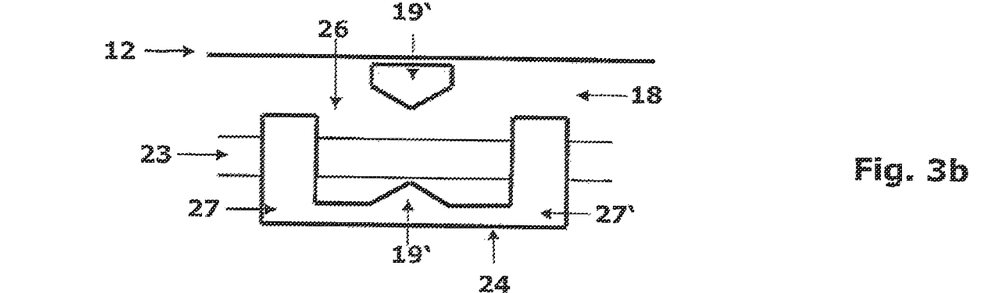

In an alternative embodiment as shown in FIG. 3b, the clamping device (18) may also be designed as a U-shaped housing (25). The top side (26) is not limited at the top and instead of the movable lever or arm, clamping elements in the form of clamping prisms (19') may be attached to the pressure plate (12) of the inside of the accommodating device (13) and/or the rigid bottom side (24) of the clamping device (18). The clamping prisms (19') on the top side (26) may be applied either reversibly or irreversibly.

In the embodiments shown in FIGS. 3a through 3d and in conjunction with FIG. 2, an activating force and/or an actuating force or a counterforce may be exerted on the middle carrier (11) of the connecting device (2) by means of the force-transfer unit (17). This results in the clamping elements and/or clamping prisms (19, 19') of the clamping device (18) being shiftable between the pressure plate (12) and the pressure-measuring unit (7) of the connecting device (2), depending on the strength of the force applied. By applying an activating force and/or an actuating force, the pressure plate (12) is moved away from the coupling surface (A) and the clamping device (18) which is inserted into the receptacle device (13) is in the open state. When an opposing force is applied, the pressure plate (12) of the accommodating device (13) however moves toward the coupling surface (A). In doing so the clamping element (19) in the form of a movable lever and/or clamping prisms (19') presses on the fluid-carrying element (23) of the clamping device (18) in such a way that the diameter of the fluid line (23) can be reduced or, in the preferably pressureless state, can be closed off completely.

Figure 3C:
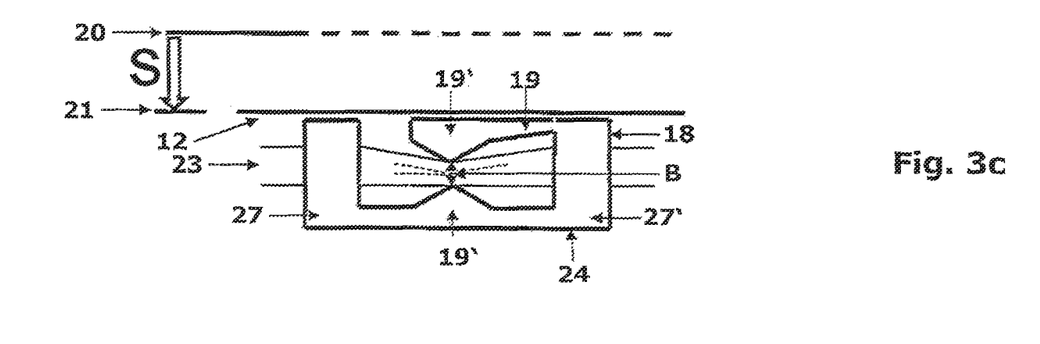
Figure 3D:
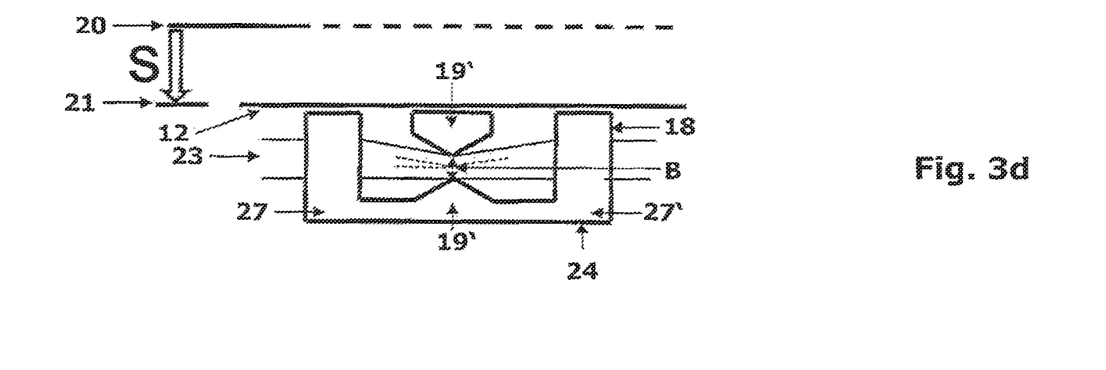

For monitoring the status of the clamping device (18), the clamping elements (19) and/or the clamping prisms (19') of the clamping device (18) are shifted over a distance (S) between a first end point (20) and a second end point (21) as shown in FIGS. 3c and 3d. The clamping state of the clamping device (18) can be ascertained by means of the analysis unit (not shown) based on the respective distance (S) travelled and detected by the length-measuring unit (15), and it is possible to ascertain whether the clamping device (18) is in an open state (FIGS. 3a, 3b) or in a closed state (FIGS. 3c, 3d) and/or in an intermediate position.

The distance (S) can be defined by the distance between the clamping elements and/or prisms (19, 19') of the clamping device (18) in the open state and the clamping element and/or prisms (19, 19') of the clamping device (18) in the closed state can be detected by means of a length-measuring unit (15). The distance (S) is also defined by the dimensions of the clamping device (18) and those of the accommodating device (13).

In a special embodiment, the maximum distance between the clamping device (18) in the open state and the clamping device (18) in the closed state can be limited structurally to prevent mechanical damage of the fluid-carrying element (23) in the form of a flexible tubing due to an excessively high force acting on the flexible tubing.

In the case of a structural limitation between the clamping device (18) in the open state and the clamping device (18) in the closed state, it may be derived from the dimensions of the clamping device (18) and the tubing cross section of the fluid-carrying element (23).

The value for the structural limitation beyond which the flexible tubing should not be unclamped again corresponds to twice the wall thickness of the flexible tubing. To reliably ensure a complete interruption in the fluid path, this value of the double tubing wall thickness for the structural limitation may be further reduced by another 40% to 60%, preferably by 5% to 10%, especially preferably by 10% to 40%. The length of the structural limitation is marked with reference notation (B) in FIG. 3c and 3d.

Figure 4:
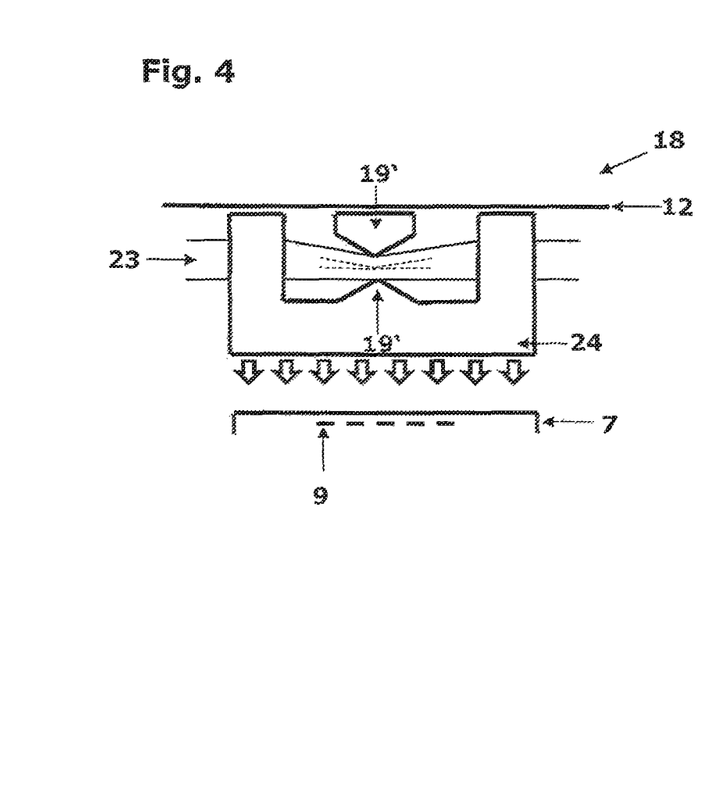
FIG. 4 illustrates schematically how a rigid area of a lower side of the clamping device cooperates with the pressure-measuring unit.

FIG. 4 shows schematically the force distribution on the pressure-measuring unit (7). By the application of a force, for example, for closing the clamping device (18), the force can be transferred from the pressure plate (12) to the clamping elements (19) and/or the clamping prisms (19'). Since the lower side (24) of the clamping device (18) is bordered by a rigid area, this leads to a uniform distribution of force over the pressure-measuring unit (7). The pressure-measuring unit (7) serves here only as a support for the lower side (24) of the clamping device (18) which is designed to be rigid, so that a distance (S) can be detected by means of a length-measuring unit (15). The pressure-sensitive membrane (9) of the pressure-measuring unit (7) is not used here.

Through the connecting device (2) which has been adapted according to the invention, this is proven by means of a clamping device (18) and a length-measuring unit (15) for monitoring the status of the clamping device (18) with a new functionality as the original functionality, which results in the advantageous effects of the invention.

Figure 5A:
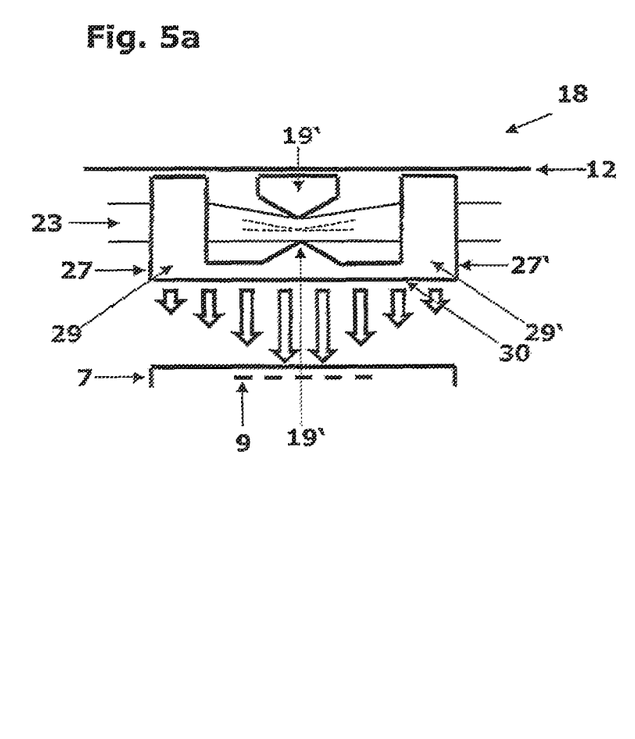
FIG. 5a shows schematically how a partially flexible lower side of the clamping device interacts with the pressure-sensitive membrane of a pressure-measuring unit.

In an especially preferred embodiment like that shown in FIG. 5a, the connecting device (2) may be designed so that, in addition to the monitoring of the status of the clamping device (18) by means of a length-measuring unit, a measurement of the clamping force can also be performed by means of the pressure sensitive membrane (9) of the pressure-measuring unit (7).

The clamping device (18) may therefore be equipped with a lower side (24) which is designed to be partially flexible and which faces the pressure-sensitive membrane (9) of the pressure-measuring unit (7). The clamping device (18) may preferably be integrated into a housing (25), as shown in FIG. 1. The lower side (24) of the clamping device (18) may also have a rigid bottom area (29, 29') and a flexible bottom area (30) instead of a continuous rigid side. The pressure-measuring unit (7) here serves first as a support for the rigid bottom area (29, 29') of the lower side (24) of the clamping device (18) when a clamping force acts on the latter. The clamping forces or closing forces are therefore distributed uniformly on the rigid bottom area (29, 29') of the clamping device (18). By means of a length-measuring unit (15) it is therefore possible to detect the precise distance (S) travelled and to draw a conclusion about the open or closed status of the clamping device (18) by means of an analysis unit (not shown).

The rigid bottom area (29, 29') may be formed by the side holders (27, 27') or designed in the form of a rigid ring, which is connected to the side holders (27, 27') and thus may be a part of the lower side (24). A flexible bottom area (30) in the form of a flexible membrane is connected to the rigid bottom area (29, 29'). This membrane can be attached to the rigid bottom area (29, 29') by welding, gluing, clamping or flanging. The clamping effect is achieved by means of clamping elements/clamping prisms (19, 19') as already described above. The clamping force, which is transferred from the liquid-carrying element (23) over the flexible bottom area (30) of the lower side (24), can be received by the pressure-sensitive membrane (9) of the pressure-measuring part (7) and can be determined by means of an analysis unit (not shown).

In another preferred embodiment, the clamping device (18) can be manufactured in one piece as an injection-moulded part. In doing so, the flexible bottom area (30) can be implemented by a reduction in wall thickness of the lower side (24) from the outside toward the centre. The size of the flexible bottom area (30) of the lower side (24) may be coordinated with the area covered by the pressure-sensitive membrane (9) in the pressure-measuring unit (7). With a greater reduction in the wall thickness toward the centre of the flexible bottom area (30), this leads to an intensified characterization of the force transmission profile. Here again, the clamping force is determined as already described above.

Figure 5B:
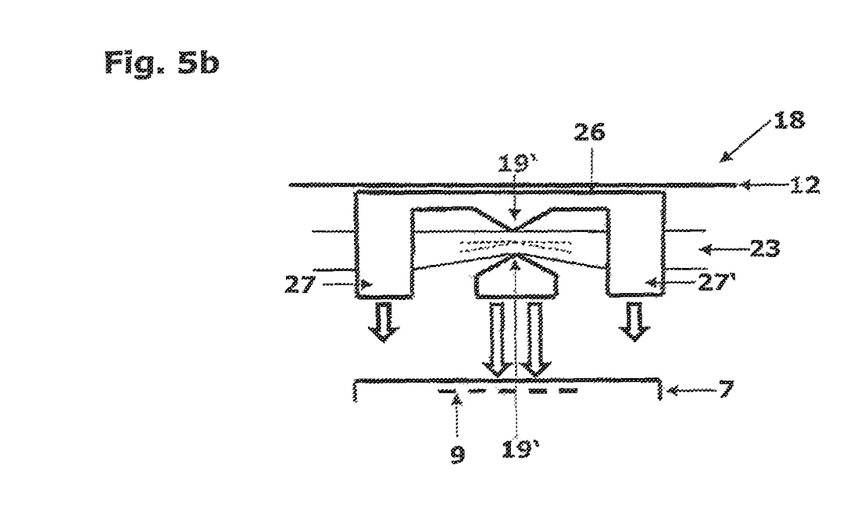
FIG. 5b shows schematically a U-shaped clamping device with separate clamping prisms, elements on the pressure-measuring unit.

FIG. 5b shows an especially preferred embodiment. The clamping device (18) may also be designed in a U shape wherein the clamping device (18) may be bordered by a rigid upper side (26). The side facing the pressure plate (12) is to be understood as the upper side (26). The rigid upper side (26) may have clamping elements in the form of clamping prisms (19') as already shown in FIGS. 3b and 3d. As the counterpart to the clamping prism (19') on the rigid upper side (26) of the clamping device (18), another clamping prism (19') may also be arranged as part of the clamping device (18) on the pressure-measuring unit (7), in particular on the pressure-sensitive area of the pressure-measuring unit (7). The clamping prism (19') is preferably reversibly locked on the pressure-measuring unit (7) in that it can be placed on diameters engaging with the pressure-measuring unit (7) and can be locked in position there to ensure a secure seating. However, the clamping prism (19') may also be mounted on the pressure-measuring unit (7) with a slip-proof lower side or a detachable adhesive layer. Therefore an arrangement (1) can be retrofitted quickly, easily and reliably for external function devices (4) with a clamping device monitoring the status.

The holders (27, 27') in this embodiment serve as a support for the pressure-measuring unit (7). A monitoring of the status of the clamping device (18) can be accomplished as already explained with regard to FIG. 5a by measuring a distance (S) by means of a length-measuring unit (15) and/or a pressure-measuring unit (7) by measuring a clamping force or a closing force via at least one of the clamping prisms (19') mounted on the pressure-sensitive membrane (9) in order to determine whether the clamping device (18) is in an open or closed state or in an intermediate position.

To determine the open and/or closed state of a clamping device (18), thus two measurement methods, which operate independently of one another are available. These two methods may be used individually or in combination. The combination of the two possibilities offers additional security for the patient, especially in the medical field.

Due to the alternative embodiment of the connecting device (2) adapted according to the invention, it is expanded by the additional function of the measurement of a clamping force or a closing force as a new functionality in addition to the monitoring of the status of the clamping device (18) by means of a length-measuring unit (15) due to the flexible bottom area (30) of the clamping device (18).

Figure 6A:
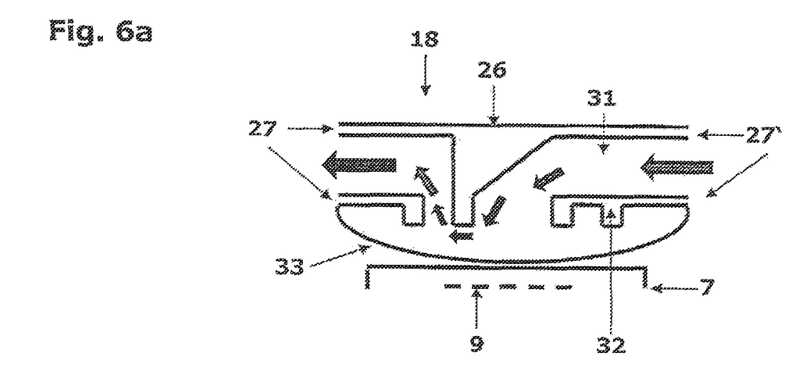
FIGS. 6a and 6b shows schematically a clamping device in the open state with flow through it as well as in the closed state, with a flexible lower side and an additional option of pressure measurement within the clamping device by means of the pressure-sensitive membrane of the pressure-measuring unit.

In a second embodiment as shown schematically in FIG. 6a, the clamping device (18) may have as the fluid carrying element (23) a flow-through chamber (31), which at the same time also represents the housing (25) of the clamping device (18). The flow-through chamber (31) contains a lower side (24), which has sealing contours (32) as clamping elements or clamping prisms (19, 19'). The lower side (24) facing the sealing contours (32) may be sealed by a flexible membrane (33). The upper side (26), which is directed toward the pressure plate (12), is preferably bordered by a rigid wall. The holders (27, 27') arranged on the sides are advantageously also designed to be rigid and form a flow connection in the form of a tube, a pipe, a channel or the like that can be connected to an arrangement (1) upstream and downstream from the flow-through chamber (31).

In the open state, the membrane (33) is not in fluid tight contact with the bottom side of the sealing contours (32) so that an intermediate space is formed between the membrane (33) and the sealing contours (32). The fluid flowing into the flow-through chamber (31) flows around the sealing contours (32) and thus permits a fluid flow.

The sealing contours (32) may be formed by at least two rings in the housing, which are separated from one another by an intermediate space. The sealing contours (32) in the flow-through chamber (31) of the clamping device (18) are preferably arranged concentrically, so they may be designed to be circular or may deviate from the circular shape and are arranged at the same height on the membrane side.

The membrane (33) may be glued, welded, clamped or flanged to the housing (25) of the clamping device (18) at the lower side (24), preferably on the outermost ring of the sealing contour (32).

Figure 6B:
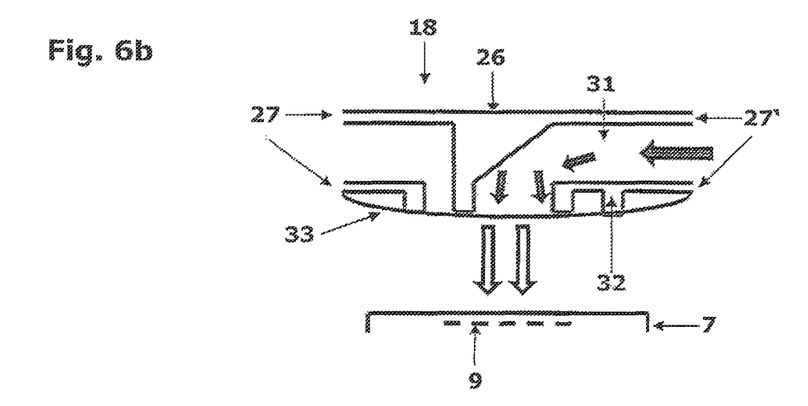

A clamping effect is achieved by the flexible membrane (33) pressing against, the sealing contours (32) as shown in FIG. 6b. As already explained above, an activating force and/or an actuating force or an opposing force may be exerted on the middle carrier (11) of the connecting device by means of a force-transfer unit (17). This results in the flexible membrane (33) being clamped to different extents between the lower edge of the sealing contours (32) and the pressure-measuring unit (7) of the connecting device (2), depending on the strength of the force applied by the accommodating device (13). The pressure plate (12) is moved away from the coupling surface (A) due to the application of an activating force and/or an actuating force, and the clamping device (18), which has been inserted into the accommodating device (13), is converted to an open state. However, when an opposing force is applied, the pressure plate (12) of the accommodating device (13) moves toward the coupling surface (A). The flexible membrane (33) of the clamping device (18) is pressed against the sealing contours (32) so that the gap between the lower edges of the sealing contours (32) and the flexible membrane (33) is reduced so that the fluid flow in the flow-through chamber (31) can be reduced or completely interrupted in the preferably pressureless state.

The clamping force or the closing force transferred to the flexible membrane (33) of the clamping device (18) is measured by the pressure-sensitive membrane (9) of the pressure-measuring unit (7). It is possible by means of an analysis unit (not shown) to ascertain whether the clamping device (18) is in an open state or a closed state or in an intermediate position.

By means of the connecting device (2) which is adapted according to the invention, this is proven by a determination of the clamping force or the closing force by the pressure-measuring unit (7) for monitoring the status of the clamping device (18) with a new functionality in comparison with the original, from which the advantageous effects of the invention result.

For the case when the pressure-measuring unit (7) presses the flexible membrane (33) tightly against the sealing contours (32) of the clamping device (18), monitoring with regard to the closed state of the clamping device (18) is also possible by detection of a distance (S) by means of a length-measuring unit (15) as already described above in detail.

In another special alternative embodiment, the connecting device (2) may be designed in such a way that in addition to monitoring with regard to a closed state of the clamping device (18) by detection of a distance (S) by means of a length-measuring unit (15), a pressure measurement can also be performed in the flow-through chamber (31) of the clamping device (18). Then the flexible bottom area (30) of the clamping device (18) may enter into contact with the pressure-sensitive membrane (9) of the pressure-measuring unit (7) in such a way that a fluid pressure in the flow through chamber (31) can be measured in the closed state, i.e., when the fluid flow in the flow-through. chamber (31) is interrupted.

On the basis of the data determined by the pressure measurement, conclusions regarding the functioning of other components of the arrangement (1) which are situated in front of the clamping device (18) of the adapted connecting device (2) can be drawn. Thus through the pressure measurement for example it is possible to check on whether an upstream pump is operating properly and/or whether the storage container has been opened or whether there is perhaps a flow resistance or leakage in the fluid-carrying lines.

Through the alternative embodiment of the connecting device (2) which has been adapted according to the invention, this device is expanded by adding the additional function of pressure measurement in addition to the monitoring of the status of the clamping device (18), this being accomplished by detecting a distance (S) by means of a length-measuring unit (15) as a new functionality.

In another alternative embodiment, the clamping devices (18) may be designed as disposable articles.

An adaptation of the existing connecting devices (2) to clamping devices (18) for connection to an arrangement (1) and for closing flow paths and for monitoring of status is explained in greater detail below on the basis of a flow chart for an extracorporeal blood treatment, in particular a plasma apheresis treatment as an example.

Figure 7:
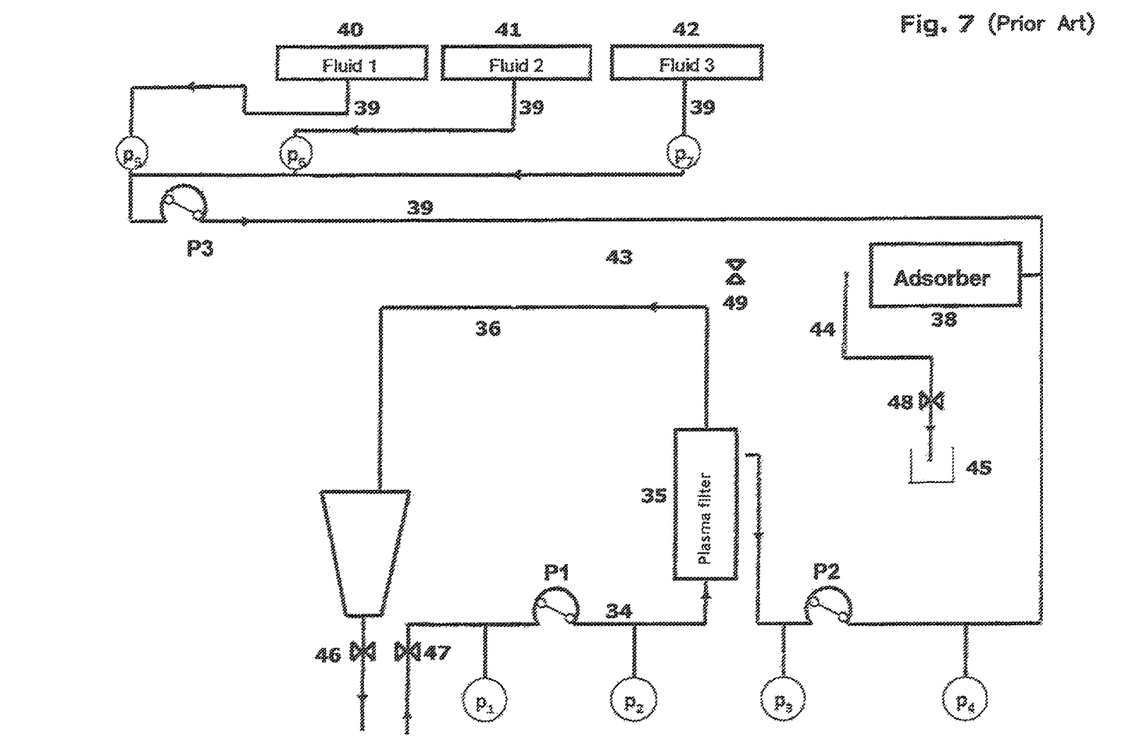
FIG. 7 shows a flow chart without adapted connecting devices as an example.

In plasma apheresis methods, as shown in FIG. 7, the patient's blood is usually passed by means of a pump (P1) through a first blood line (34) into a plasma filter (35), where the plasma is separated from the blood. The other components of blood are returned to the patient through a second blood line (36). The separated plasma passes through a plasma line (37) into an adsorber (38) where unwanted constituents are bound and the plasma thereby purified is returned to the patient through a second plasma line (43) and a second blood line (36).

To be able to ensure an optimal success of the treatment, it is important to accurately monitor the flow rate in the individual treatment sections by means of pressure measurements. Therefore, in the known arrangements (1), connecting devices (2) are provided with an external function device (4) for the pressure measurements at positions p1 through p7.

In complex plasma apheresis methods, which operate with regenerable adsorbers (38), for example, the adsorber must be purified and/or regenerated at a certain load. Regeneration of the adsorber (38) may be necessary during treatment of the patient under some circumstances. To spare the patient additional coupling and uncoupling due to a reorganization of the arrangement, the adsorber regeneration should preferably be such that it can be performed during the treatment. To do so, different solutions must be passed through the adsorber material one after the other. The required containers (40, 41, 42) with the regeneration fluid can be suspended from the fluid lines (39) for this purpose, and the individual regeneration fluids can be passed through these containers and into the adsorber (38). The constituents adsorbed from the plasma are usually washed first from the adsorber material using a strong acid. Next the adsorber material is neutralized and finally it is rinsed with a physiological solution. The used regeneration fluid is drained into a drainage container (45) through a drainage line (44).

Since the cleaning solutions are sometimes aggressively non-physiological solutions, it is absolutely necessary during regeneration for the solutions to be directed into the adsorber (38) in a certain order, and it is also absolutely essential that there not be any mixing and/or introduction of cleaning solutions into the patient during the regeneration phase. To ensure the safety of the patient during regeneration of the absorber (38), it is therefore absolutely essential that the fluid lines (39) to the regeneration fluid containers (40, 41, 42) must be reliably closable and that the clamping function must be monitorable.

The connecting devices (2), which are used in the known arrangements (1), in particular the connecting devices (2) in positions p5 through p7 in this example, are equipped with function devices (4) for measuring the pressure and therefore are not suitable for closing off fluid paths or for monitoring the status of a clamping device (18).

Since no additional clamps are available for the regeneration process in the known arrangements (1), the individual fluid lines (39) of the regeneration fluids must be closed off by means of manual clamps. To service them, the user must receive an alarm in a targeted manner during the corresponding process step and must then intervene. This type of procedure is associated with a high risk of mistakes in operation.

During the regeneration phase, the connecting devices (2) originally present in positions p5 through p7 with an external function device for the pressure measurement are not needed, but instead additional clamps are needed, so it is now possible with the adapted connecting devices (2) to insert a function device (4) with a clamping device (18) into a receptacle unit (13) and to adapt a pressure-measuring unit (7) for detection of a clamping force or a closing force and/or to adapt a length-measuring unit (15) for measurement of a distance (S) to permit automatic monitoring of the status of the clamping device (18).

Figure 8:
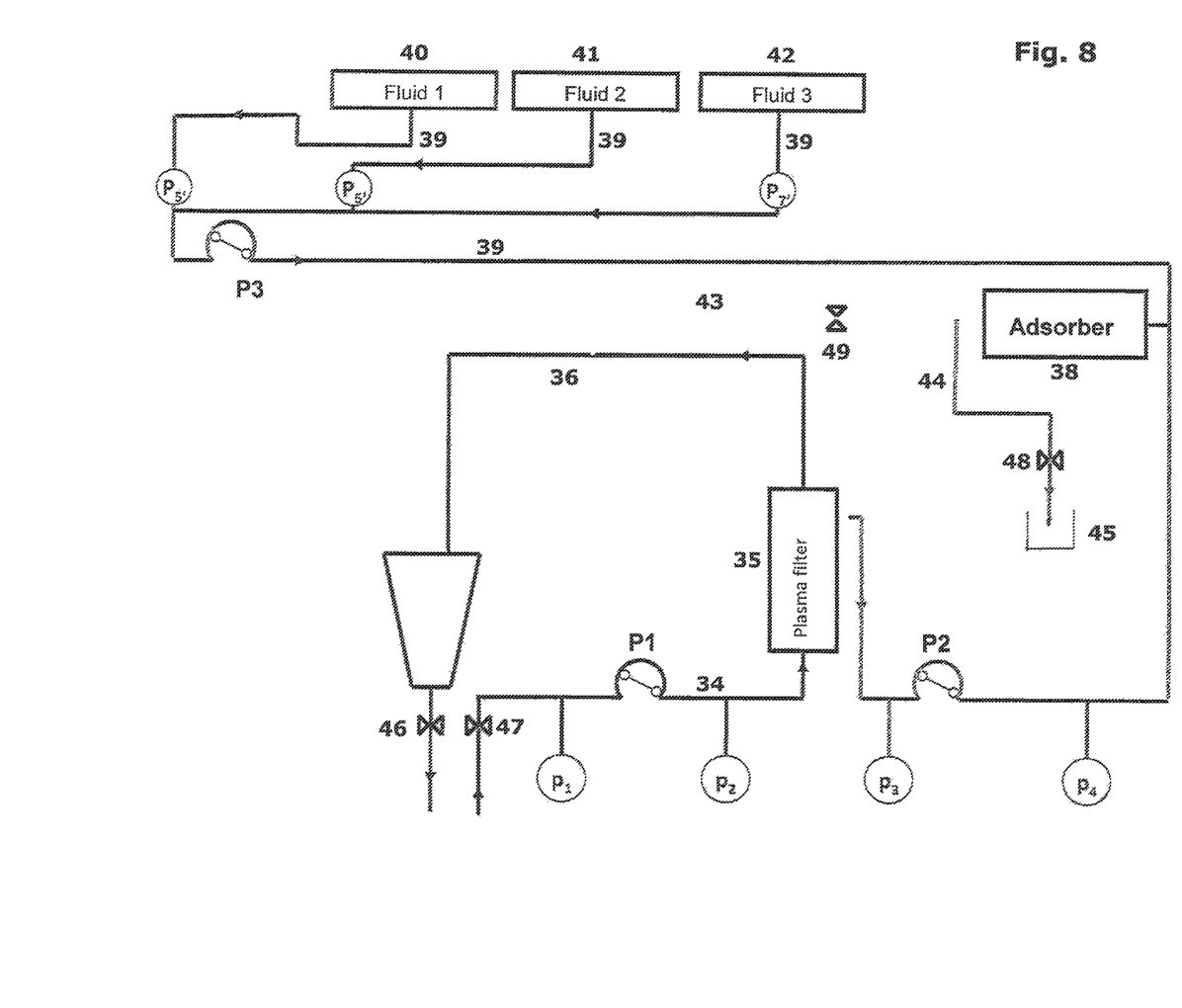
FIG. 8 shows a flow chart with connecting devices adapted by clamping devices as an example.

FIG. 8 shows the above flow chart with the adapted connecting devices (2) in positions p5', p6' and p7' as the external function devices (4) for monitoring the status of the clamping devices (18).

In addition, all the connecting devices (2) for which additional clamping devices are required, for example, for the pressure measuring devices in positions p1, p2, p3 and/or p4 can also be adapted within an arrangement (1). This may also be the case when additional dialysate solutions or drug solutions must be administered in a treatment process, a diagnostic procedure or the like.

The invention being thus described, it will be apparent that the same may be varied in many ways, Such variations are not to be regarded as a departure from the spirit and scope of the invention, and all such modifications as would be recognized by one skilled in the art are intended to be included within the scope of the following claims.

LIST OF REFERENCE NUMERALS 1 arrangement
2 connecting device
3 outer carrier
4 external function device
5 protrusion
6 inner carrier
7 pressure-measuring unit
8 connecting carrier
9 pressure-sensitive membrane of the pressure-measuring unit
10 force transfer connection
11 middle carrier
12 pressure plate
13 accommodating device
15 length-measuring unit
17 force-transfer unit
18 clamping, valve device
19, 19' clamping elements, clamping prisms °first end point
21 second end point
23 fluid-carrying element
24 lower side of the clamping device
25 housing
26 upper side of the clamping device
27, 27' side holders
29 rigid bottom area
30 flexible bottom area
31 flow-through chamber
32 sealing contours
33 flexible membrane
34 first blood line
35 plasma filter
36 second blood line
37 first plasma line
38 adsorber
39 fluid line
40, 41, 42 regeneration fluid containers
43 second plasma line
44 drainage line
45 drainage container
A coupling surface
B structural border
P1, P2, P3 pumps
p1-p7 connecting device with pressure measurement
p5', p6', p7' adapted connecting device with clamping device
S distance

What is claimed is:

1. A connecting device for connecting an external function device to an arrangement, comprising
   an accommodating device for accommodating the external function device,
   an outer carrier that includes an essentially cylindrical inner carrier and a movable middle carrier,
   at least one of a pressure-measuring unit for measuring a pressure in the external function device and
   a length-measuring unit for measuring a distance (S), and
   a force-transfer unit for continuous displacement of the movable middle carrier along the distance (S),
   the external function device being a clamping device for closing off a flow path,
   the clamping device including at least one of a clamping element and a clamping prism,
   the pressure-measuring unit being configured to detect a clamping force and
   the length-measuring unit being configured to measure a distance (S) between a first end point and a second end point,
   so as to monitor a clambing status of the clamping device.

2. The connecting device according to claim 1, wherein the clamping device includes a fluid-carrying element and the clamping element,
   the fluid-carrying element being a flexible tubing which is guided through two opposite side holders of the clamping device, and
   the clamping element being configured as hose clamp having at least one of a movable lever, an arm, and the clamping prism.

3. The connecting device according to claim 1, wherein the clamping device includes a housing, a fluid-carrying element, and the clamping element,
   the housing having an open upper side, a rigid lower side, and two opposite side holders,
   the fluid-carrying element being a flexible tubing, and
   the clamping prism being mounted on an inside of the accommodating device in the rigid lower side of at least one of the clamping device and a pressure plate.

4. The connecting device according to claim 1, wherein the distance (S) between the first end point and the second end point is defined by a distance between the clamping element and the clamping prism in an open state and the clamping element and the clamping prism in a closed state.

5. The connecting device according to claim 4, wherein the distance (S) between the clamping device in the open state and the clamping device in the closed state is defined by dimensions of the clamping device and of the accommodating device.

6. The connecting device according to claim 5, wherein the distance (S) between the clamping device in the open state and the clamping device in the closed state is limited by a structural limitation (B) associated with dimensions of the clamping device and a cross section of the tubing of the fluid-carrying element.

7. The connecting device according to claim 1, wherein a lower side of the clamping device has a rigid bottom area and a flexible bottom area.

8. The connecting device according to claim 7, characterized in that the flexible bottom area is connected to the rigid bottom area by welding, gluing, clamping, or flanging.

9. The connecting device according to claim 1, wherein the clamping device includes a housing, a fluid-carrying element, and the clamping element,
   the fluid-carrying element being a flow-through chamber,
   the clamping element being configured as sealing contours in the housing, and
   the housing having a lower side, which faces the sealing contours and is bordered by a flexible membrane, and upper side, which is formed by a rigid wall.

10. The connecting device according to claim 9, wherein the sealing contours are formed by at least two rings in the housing.

11. The connecting device according to claim 9, wherein the sealing contours are arranged concentrically in the housing, are circular or substantially circular in shape, and are arranged at a same height on a membrane side of the housing.

12. A method of connecting at least one flexible function device in a connecting device to an arrangement according to claim 1, said method comprising displacing the movable middle carrier along the distance (S) between the first end point and the second end point with the force-transfer unit, such that the distance (S) travelled is detected by the length-measuring unit and/or the clamping force or a closing force is detected by the pressure-measuring unit, and monitoring the clamping status of the clamping device with an analysis unit.

13. The method according to claim 12, wherein the distance (S) is detected by the length-measuring unit, the clamping force is measured over a flexible bottom area by a pressure-sensitive membrane of the pressure-measuring unit, and the monitoring of the clamping status of the clamping device is effected with the analysis unit.

14. The method according to claim 12, wherein a fluid pressure in a fluid-carrying element is determined in a closed state by the pressure-measuring unit via the clamping device.

15. A clamping device which is adjusted for accommodating and for functioning in a connecting device for connection to an arrangement according to claim 1.

* * * * *